US009052296B2

(12) United States Patent
Wu et al.

(10) Patent No.: US 9,052,296 B2
(45) Date of Patent: Jun. 9, 2015

(54) ANALYSIS OF HYDROCARBON LIQUID AND SOLID SAMPLES

(71) Applicants: Chunping Wu, Whitehouse Station, NJ (US); Clifford C. Walters, Milford, NJ (US); Kuangnan Qian, Skillman, NJ (US)

(72) Inventors: Chunping Wu, Whitehouse Station, NJ (US); Clifford C. Walters, Milford, NJ (US); Kuangnan Qian, Skillman, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 14/071,712

(22) Filed: Nov. 5, 2013

(65) Prior Publication Data
US 2014/0165701 A1    Jun. 19, 2014

Related U.S. Application Data

(60) Provisional application No. 61/738,738, filed on Dec. 18, 2012.

(51) Int. Cl.
*G01N 33/24*   (2006.01)
*G01N 27/62*   (2006.01)
*G01N 30/02*   (2006.01)
*H01J 49/14*   (2006.01)

(52) U.S. Cl.
CPC .............. *G01N 30/02* (2013.01); *G01N 27/62* (2013.01); *G01N 33/241* (2013.01); *H01J 49/142* (2013.01)

(58) Field of Classification Search
CPC ....... G01N 27/62; G01N 30/02; G01N 33/24; G01N 33/241; H01J 49/0431
USPC ............ 436/60, 139, 173, 174; 250/281, 282; 73/23.38, 152.04, 152.11
See application file for complete search history.

(56) References Cited

U.S. PATENT DOCUMENTS

| 8,044,346 | B2* | 10/2011 | Kostiainen et al. ........... 250/288 |
| 2005/0230635 | A1 | 10/2005 | Takats et al. |
| 2008/0067352 | A1 | 3/2008 | Wang |
| 2011/0165695 | A1* | 7/2011 | Chan et al. ..................... 436/175 |
| 2012/0119079 | A1* | 5/2012 | Ouyang et al. ................ 250/282 |
| 2012/0153139 | A1 | 6/2012 | Qian et al. |
| 2013/0344610 | A1* | 12/2013 | Cooks et al. ................... 436/141 |

OTHER PUBLICATIONS

Wu et al. Journal of the American Society of Mass Spectrometry, vol. 21, Nov. 13, 2009, pp. 261-267.*
Van Berkel et al. Analytical Chemistry, vol. 77, No. 5, Mar. 1, 2005, pp. 1207-1215.*

(Continued)

*Primary Examiner* — Maureen Wallenhorst
(74) *Attorney, Agent, or Firm* — Larry E. Carter; Andrew T. Ward

(57) ABSTRACT

Systems and methods are provided for analysis and/or profiling of petroleum samples. The systems and methods allow for compositional analysis of samples using techniques that can be implemented outside of a laboratory setting, such as in a refinery or even at a petroleum or hydrocarbon source. The techniques are enabled by using desorption electrospray ionization as a method for generating ions for detection by mass spectroscopy. Desorption electrospray ionization can be used to generate ions for detection from a liquid or solid petroleum (or other hydrocarbon) sample with minimal sample preparation. For solid samples, the technique can also be used to identify changes in composition of a petroleum sample relative to a dimension of the solid sample.

15 Claims, 10 Drawing Sheets

(56) References Cited

OTHER PUBLICATIONS

Sokol et al. Prep. Pa.-Am. Chem. Soc., Div Fuel Chem., 2010, vol. 55(2), p. 180.*

Eckert et al. Analytical Chemistry, vol. 84, Dec. 13, 2011, pp. 1517-1525.*

PCT Application No. PCT/US2013/072155, Search Report and Written Opinion, Form PCI/ISA/220, dated Mar. 10, 2014, 8 pages.

* cited by examiner

ANALYSIS OF HYDROCARBON LIQUID AND SOLID SAMPLES

FIELD OF THE INVENTION

This invention provides methods for characterizing the composition of hydrocarbon or petroleum samples, including liquid and solid samples of hydrocarbon or petroleum fraction, and/or for characterizing syngenetic petroleum within source rocks or migrated petroleum on rock surfaces.

BACKGROUND OF THE INVENTION

Petroleum samples are complicated hydrocarbon mixtures containing paraffins, cyclic paraffins, multiring aromatics, and various heteroatomic hydrocarbons (most commonly O, S, and N). Produced petroleums contain molecules of a wide boiling point range from highly volatile $C_{1-4}$ hydrocarbon gases to nonvolatile asphaltenes. Analysis of petroleum composition of various boiling ranges is valuable for improving the operation of many subsequent processes.

Detailed analysis of the composition of a petroleum sample is typically performed under controlled conditions in a laboratory setting. Due to the complexity of hydrocarbon or petroleum samples, analysis of composition usually involves a variety of sample preparations, such as performing an initial separation of a sample based on boiling point and/or chromatographic separation. Analysis of a whole crude sample is typically limited to bulk property characterization, such as determining a boiling point profile, an API gravity, or a sulfur content In some instances, petroleum is derived from organic-rich sedimentary rocks. As these source rocks are heated, insoluble kerogen is converted to hydrocarbon and non-hydrocarbon products that are either expelled as petroleum or retained as soluble bitumen. The expelled petroleum migrates through other strata where it may leave surface stains or accumulate in porous reservoir rocks into accumulations.

SUMMARY OF THE INVENTION

In an embodiment, a method for analyzing a hydrocarbon sample is provided. The method includes obtaining a solid matrix containing a hydrocarbon sample; impinging a solvent on the prepared hydrocarbon sample having a surface at an angle between about 30° and about 60° relative to the surface, the solvent comprising a stream of solvent droplets, the solvent comprising a non-polar compound and a polar compound; capturing droplets desorbed from the surface at an inlet conduit for a mass spectrometer, the captured droplets including one or more compounds from the hydrocarbon sample; and generating at least one mass spectrum based on the one or more compounds from the hydrocarbon sample.

In an embodiment, a method for analyzing a hydrocarbon sample is provided. The method includes preparing a hydrocarbon sample having a surface; impinging a solvent on the prepared hydrocarbon sample having a surface at an angle between about 30° and about 60° relative to the surface, the solvent comprising a stream of solvent droplets, the solvent comprising a non-polar compound and a polar compound; capturing droplets desorbed from the surface at an inlet conduit for a mass spectrometer, the captured droplets including one or more compounds from the hydrocarbon sample; and generating at least one mass spectrum based on the one or more compounds from the hydrocarbon sample.

DETAILED DESCRIPTION OF THE EMBODIMENTS

Overview

Figure 1:
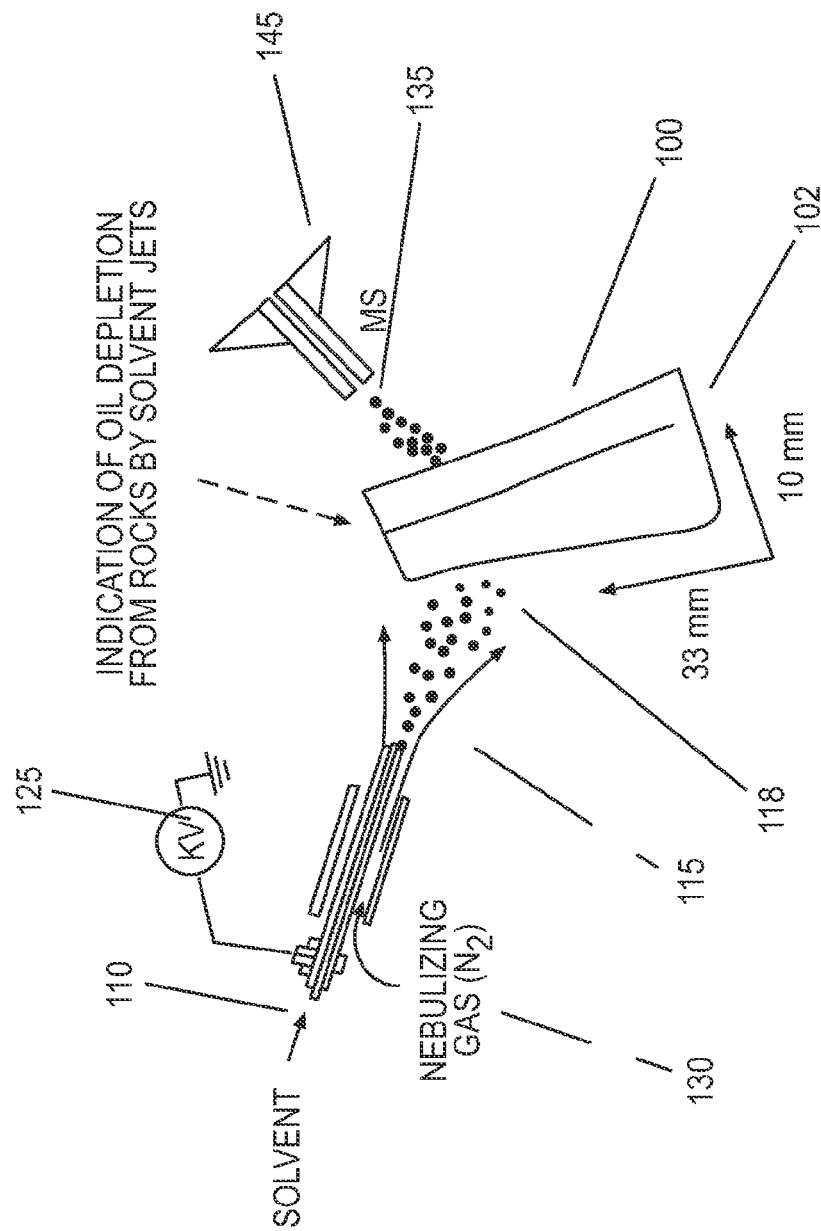
FIG. 1 schematically shows an example of a system for performing desorption electrospray ionization in order to generate ions for detection by a mass spectrometer.

In various embodiments, systems and methods are provided for analysis and/or profiling of petroleum samples. The systems and methods allow for compositional analysis of samples using techniques that can be implemented outside of a laboratory setting, such as in a refinery or even at a petroleum or hydrocarbon source. The techniques are enabled by using desorption electrospray ionization as a method for generating ions for detection by mass spectroscopy. Desorption electrospray ionization can be used to generate ions for detection from a liquid or solid petroleum (or other hydrocarbon) sample with minimal sample preparation. In particular, the ionization technique can be applied under ambient conditions, as opposed to requiring preparation of a sample by placing it in a reduced pressure environment. For solid samples, the technique can also be used to identify changes in composition of a petroleum sample relative to a dimension of the solid sample.

For many types of petroleum sources, the petroleum or hydrocarbons are located within a solid matrix prior to extraction. Conventionally, the amount of organic material in a solid matrix can be determined by techniques such as gamma ray analysis. However, this type of analysis cannot provide compositional information about a sample. Instead, compositional information regarding the compounds in a solid matrix is obtained by extracting the compounds from the matrix using solvent extraction. The extracted compounds can then be prepared for analysis using conventional methods, such as performing a chromatographic separation followed by mass spectrometry on at least a portion of the material derived from the separation. While conventional solvent extraction, separation, and analysis methods are effective for determining compositional information for a sample, other information is lost during the analysis. For example, the distribution of compounds within the solid matrix may vary spatially, such as varying with respect to the original depth of the solid matrix.

Any spatial variance in the composition is lost when the petroleum sample is extracted to form the liquid sample for analysis.

The systems and methods described herein can allow for direct analysis of a petroleum or hydrocarbon sample. Instead of requiring one or more initial preparation steps to dissolve a sample in a carrier solvent, the sample can be directly ionized and volatilized using an electrospray ionization method. This results in a single process where a sample is solvated by a solvent, charge is transferred to the compounds in the solvated sample, and the solvated sample is volatilized for characterization by mass spectrometry. For solid samples, the method also allows spatial changes in sample composition to be captured along at least one dimension.

Petroleum or Hydrocarbon Samples for Analysis

In this description, reference may be made to hydrocarbon streams, hydrocarbon samples, and/or hydrocarbon mixtures. Hydrocarbon streams, samples, or mixtures are defined herein to include streams, samples, or mixtures containing heteroatoms. As understood by those of skill in the art, a typical mineral petroleum feedstock often includes compounds containing heteroatoms, such as (but not limited to) compounds containing sulfur, nitrogen, trace metals, and/or oxygen. Unless it is specifically indicated otherwise, hydrocarbon streams, samples, or mixtures are defined to include streams, samples, or mixtures containing compounds that include such heteroatoms. Thus, even though a typical petroleum sample contains atoms other than carbon and hydrogen, such a petroleum sample is included in the definition of a hydrocarbon sample.

In this discussion, reference will be made to analyzing petroleum samples and/or hydrocarbon samples. A petroleum and/or hydrocarbon sample can be obtained in any convenient manner. An initial source for a sample can correspond to a raw or virgin mineral feed, a non-conventional feed such as a synthetic crude or a biologically derived oil, an output from a refinery process, or a combination of any of the above. Additionally or alternately, a petroleum or hydrocarbon sample can correspond to either a liquid sample or a sample within a solid matrix. A core sample taken from potential or existing well location or shale extraction location is an example of a petroleum sample within a solid matrix. Other examples in a solid matrix include source rocks and oil shale.

The boiling range of a petroleum and/or hydrocarbon sample can be any convenient boiling range, so long as the sample has a sufficiently low vapor pressure under ambient conditions to be suitable for ionization using desorption electrospray ionization. For full range petroleum samples, compounds with a boiling point of 40° C. or less may be more difficult to characterize, as the compounds may be substantially lost due to vaporization without ionization. Otherwise, the sample can correspond to a whole or partial crude oil sample, or a fraction corresponding to one or more output portions from a separation. Examples of fractions from a separation include distillate boiling range fractions, lubricant base oil boiling range fractions, and heavy oil fractions. The initial boiling point of the sample can be at least about 100° C., or at least about 200° C., or at least about 300° C., or at least about 400° C. The final boiling point of the sample can be about 600° C. or less, or about 500° C. or less, or about 400° C. or less, or about 300° C. or less.

For a liquid petroleum sample source, a sample can be prepared for analysis by placing the sample on a substrate. This provides a surface to facilitate analysis of the sample. A suitable substrate can be substantially level in a region where the liquid sample is deposited. Examples of potential substrates include, but are not limited to, filter paper, a polymer substrate such as polytetrafluoroethylene substrate or a polyvinylidene fluoride substrate, or a silica gel type substrate such as a sample substrate for performing high pressure thin film liquid chromatography (HP-TLC). For selection of a substrate, one desirable property is a substrate that will be "wetted" by the hydrocarbon sample. If the hydrocarbon sample does not wet the substrate well, the sample will ball up to form droplets on the surface. These droplets can have a tendency to be blown off of the substrate without be ionized and vaporized. By contrast, a surface that is wetted well by the hydrocarbon sample, and that has sufficient porosity, will tend to adsorb the hydrocarbon sample. For a substrate surface that is wetted well by the hydrocarbon sample, the hydrocarbon sample is less likely to be blown off of the surface without undergoing the desired desorption and ionization process. Additionally, at least a portion of the sample may enter the pores of the substrate surface. It is believed that portions of the hydrocarbon sample that enter the pore network of a substrate surface will still be available for solvation by the solvent used for desorption and ionization. This further reduces the likelihood of the hydrocarbon sample being removed from the surface to a degree that would prevent characterization using the method.

Optionally, the petroleum or hydrocarbon sample can be mixed with a preparation solvent prior to deposition of the sample on the substrate. A suitable preparation solvent can be a non-polar solvent. Preferably, the non-polar solvent is the same as a non-polar solvent compound in the solvent used for desorption electrospray ionization of the sample. An example of a suitable non-polar solvent is toluene, or any other solvent identified as a suitable non-polar solvent for desorption electrospray ionization.

For examples using HP-TLC substrates, the substrates used were Nano-Silica XHL High Performance (HP)-TLC plates (glass backed, 200 μm stationary phase) purchased from Sorbent Technologies, Inc. (Atlanta). When using HP-TLC plates as the substrate, petroleum samples were diluted to 10,000 ppm in toluene. 1 μL of the sample solution was then placed on the HP-TLC plate.

For a petroleum (hydrocarbon) sample in a solid matrix, the sample can be prepared by obtaining a sample that has a substantially flat surface. The sample can be obtained by using a sample that already has a substantially flat surface, or the sample can be cut or otherwise machined to have a substantially flat surface. For example, a cylindrical solid matrix with a diameter of about 4 inches to 6 inches can be cut in half to produce a flat surface. The substantially flat surface is valuable for reducing or minimizing the amount of flow or pooling of solvent on the surface during analysis due to variations in the shape of the sample. A substantially flat surface can be further polished or sanded if desired, but this is not necessary for characterizing the petroleum (hydrocarbon) sample in the solid matrix. A substantially flat surface can correspond to a surface of a substrate or sample matrix that has a roughness of 1 mm or less. Cutting, machining, or polishing a sample at a time relatively close to the time for analysis may have an additional benefit in increasing the likelihood that petroleum (hydrocarbons) from the petroleum sample will be available in the portion of the pore network near the surface of the sample. Preferably, the substantially flat surface of the sample is relatively flat along a direction that corresponds to a direction for determining spatial variations of the petroleum in the solid matrix. For example, if the solid matrix corresponds to a core sample, the substantially flat direction can be aligned with (i.e., be approximately parallel to) the corresponding depth for the core sample, in order to determine variations in the petroleum sample relative to the potential depth of a well. When analyzing shale core samples in the examples described herein, the core (solid matrix) was pre-cut and optionally polished if needed to achieve a sufficiently flat substrate.

Analysis of Petroleum Samples with Desorption Electrospray Ionization Mass Spectrometry In various embodiments, desorption electrospray ionization mass spectrometry can be used to characterize a liquid petroleum sample or a petroleum sample in a solid matrix. One advantage of using desorption electrospray ionization for forming ions for detection is that the desorption and ionization can be performed at ambient pressure. This simplifies sample preparation. Additionally, the ionization method is a "soft" ionization method that results in a reduced or minimal amount of fragmentation of the compounds within the sample.

As an initial step, a solvent is passed through an electric field to produce a charged solvent. For example, a conduit or tube for delivering the solvent can be a charged conduit. As the solvent exits the conduit, the solvent will acquire a charge. A syringe is another example of a suitable conduit. The solvent then impinges on the sample for analysis, such as by spraying the solvent onto the sample for analysis. The solvent can impinge on the surface including the hydrocarbon sample by any convenient method, such as by using a nebulizing gas to form droplets of the charged solvent that spray onto the surface based on the momentum of the solvent as it exits the delivery conduit. As the solvent strikes the petroleum sample, at least a portion of the hydrocarbon sample is dissolved into the charged solvent. The momentum from the solvent spray can then contribute to causing solvent droplets that contain the sample as a solute to be desorbed. These solvent droplets containing at least a portion of the sample can be captured by an inlet conduit for a mass spectrometer. A reduced pressure can be used at an inlet capture conduit for the mass spectrometer to assist with directing the desorbed solvent/solvated sample into the mass spectrometer.

As the solvent with dissolved sample travels to and/or into the mass spectrometer, the charge is transferred from solvent molecules to molecules from the sample. This results in ionization of the sample in manner that reduces the likelihood of fragmentation for the compounds in the sample.

FIG. 1 schematically shows an example of an apparatus for desorbing and ionizing a sample. In FIG. 1, a petroleum sample in a solid matrix 100 is positioned for analysis. In the example shown in FIG. 1, the surface of the solid matrix where the solvent impinges has a length of 33 mm and a width of 10 mm. Of course, in various embodiments samples with any convenient surface size may be used. A liquid sample on a substrate can also be used in place of a sample in a solid matrix. A solvent 110 is passed through a syringe 115 that is directed at the solid matrix 100. An electric charge is applied 125 to the syringe 115 so that the solvent 110 is ionized as it exits tube 115. A nebulizing gas 130 is directed approximately in a co-axial direction with the solvent 110 in order to form droplets from the solvent flow. The nebulized solvent 118 impinges on the solid matrix 100. This results in solvation of sample compounds into the solvent. Due in part to the momentum of the nebulized solvent 118, after solvation of sample compounds the solvent droplets are desorbed from the surface of solid matrix 100. The desorbed droplets are then captured by an inlet 135 for a mass spectrometer 145.

In the example shown in FIG. 1, a line 102 is shown on the surface of solid matrix 100. The line 102 is a schematic representation of the path the nebulized solvent is tracing on the solid matrix. Such a line 102 may also be visible, due to depletion of the petroleum or hydrocarbon sample within the solid matrix. By scanning along a line, a spatial profile of the composition of the sample can be determined.

In various embodiments, improving or optimizing the conditions for desorption and ionization can improve the detection of compounds within a sample. It has been determined that the ionization is largely affected by the voltage applied on the syringe needle or other conduit used for dispensing the solvent. Higher voltages applied to the conduit can result in increased sensitivity for detection in the mass spectrometer. An example of a suitable voltage to apply to a conduit is about 5 KV.

The angle for impinging the solvent onto the surface for analysis can be an angle suitable for allowing the momentum of the impinging solvent to assist with desorption of solvent droplets that are already on the surface. Suitable angles for the impinging solvent can be from about 30° to about 60° relative to the surface. The plane for measuring the impinging angle can be a plane that is substantially parallel to the surface. If there is ambiguity about how to define a plane that is substantially parallel to the surface, the plane can instead be defined as a plane that is tangential to the location on the surface where the solvent is impinging. In situations where the impinging solvent is scanned across the surface, the plane can be defined as the average of the planes defined as the impinging solvent is scanned along the scanning direction.

Figure 2:
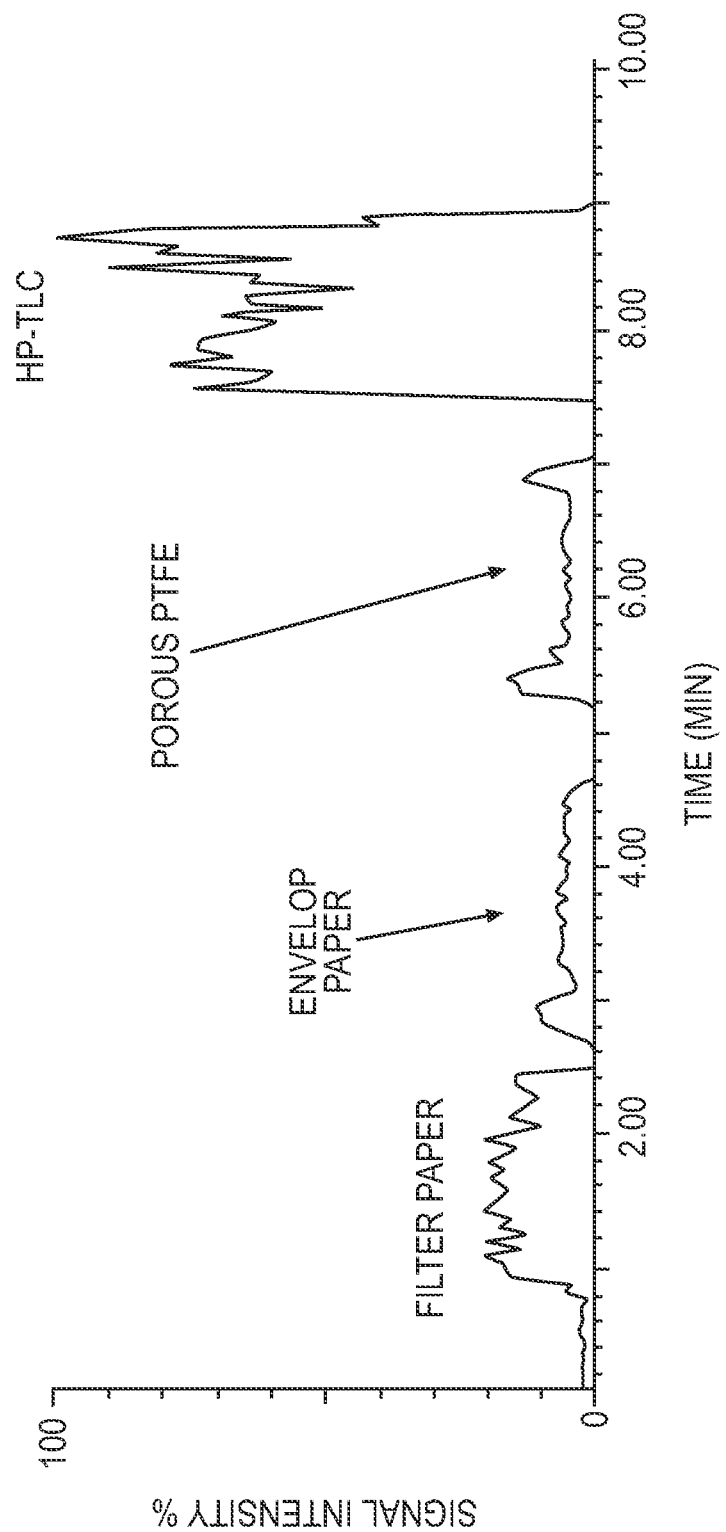
FIG. 2 shows the impact on signal intensity for various substrate types during analysis of a liquid hydrocarbon sample.

As noted above, for liquid samples the substrate that the liquid is placed on for analysis can have an impact on the signal intensity. FIG. 2 shows the signal intensity for a vacuum gas oil sample placed on various types of substrates. As shown in FIG. 2, the high pressure thin film liquid chromatography (HP-TLC) silica gel substrates provided the best signal intensity. The next best signal intensity was generated when using the filter paper substrate. Although filter paper is wetted well by petroleum samples, the vacuum gas oil sample used for the data in FIG. 2 spread out to a much greater degree than the amount of spreading for the HP-TLC substrate. This may have resulted in a lower density of the petroleum sample at any given location in the target area. The envelope paper had a similar amount of sample spread as the filter paper, but resulted in a still lower signal intensity. The PTFE substrate also resulted in a relatively low signal intensity. Unless noted otherwise, the desorption electrospray ionization examples described herein were performed using an HP-TLC slide as a substrate.

Solvents can also play an important role in desorption. Both the solubility and the vaporization of solvents can be considered. For example, if the solvent is too volatile, the solvent spot will be relatively small and it cannot efficiently desorb the sample. On the other hand, if the volatility is too low, the substrate will be too "wet", and solvation and/or desorption will be limited. Additionally, the amount of solvent to use represents a balance of factors. If too little solvent is used, the charge transfer from solvent to the sample compounds may be too low to achieve a desirable signal strength. For higher solvent flow rates, there are practical limits to the amount of solvent that can be used. The ratio of non-polar to polar solvent can be 1:2 or less, such as 1:4 or less.

For various types of vacuum gas oil samples, it has been determined that a mixture of toluene and acetonitrile in a 1:5 ratio by volume, where the mixture also includes 0.1% by volume formic acid, resulted in good sensitivity. A non-polar solvent such as toluene can facilitate the desorption of petroleum oil from rock or another solid matrix. However, non-polar compounds such as toluene are less effective as a charge carrier for the ionization of petroleum molecules. To improve charge carrier characteristics of the overall mixture of solvents, a polar solvent such as acetonitrile and a proton donor formic acid can be included in the solvent. Combining a non-polar solvent with a suitable amount of polar solvent and/or proton donor can improve the signal intensity for the detection of compounds in the sample. Examples of suitable non-polar solvents include toluene, carbon tetrachloride, xylene, benzene, chloroform, methylene chloride, and aromatic hydrocarbons that do not contain heteroatoms (i.e., that contain only carbon and hydrogen). As noted above, hydrocarbons in this description are defined to allow for heteroatoms unless otherwise specified. Examples of polar solvents include acetonitrile and alcohols containing six carbons or less such as methanol or butanol. Examples of proton donors include formic acid and other organic acids containing four carbons or less.

Figure 3A:
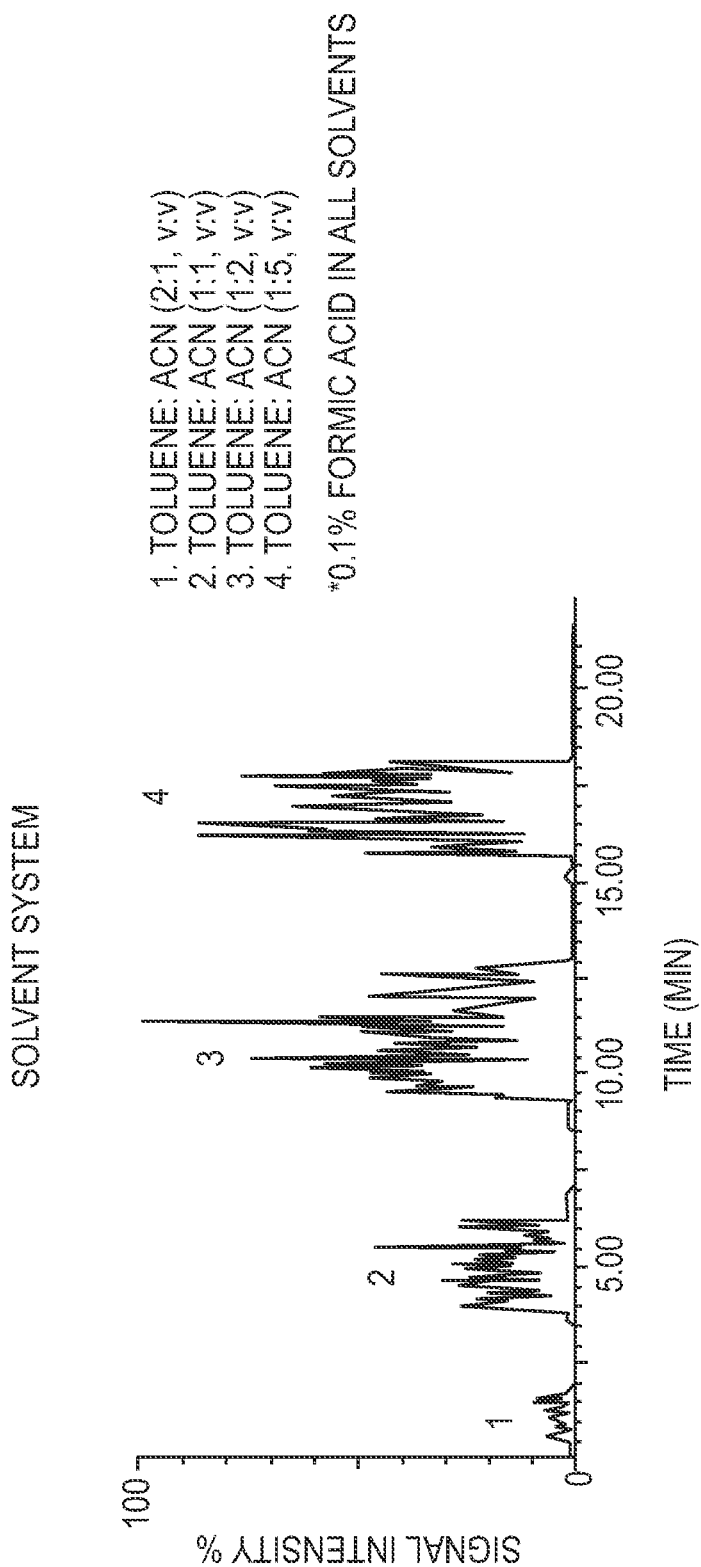
FIG. 3A and FIG. 3B show the impact on signal intensity based on variations in the solvent during analysis of a hydrocarbon sample.
Figure 3B:
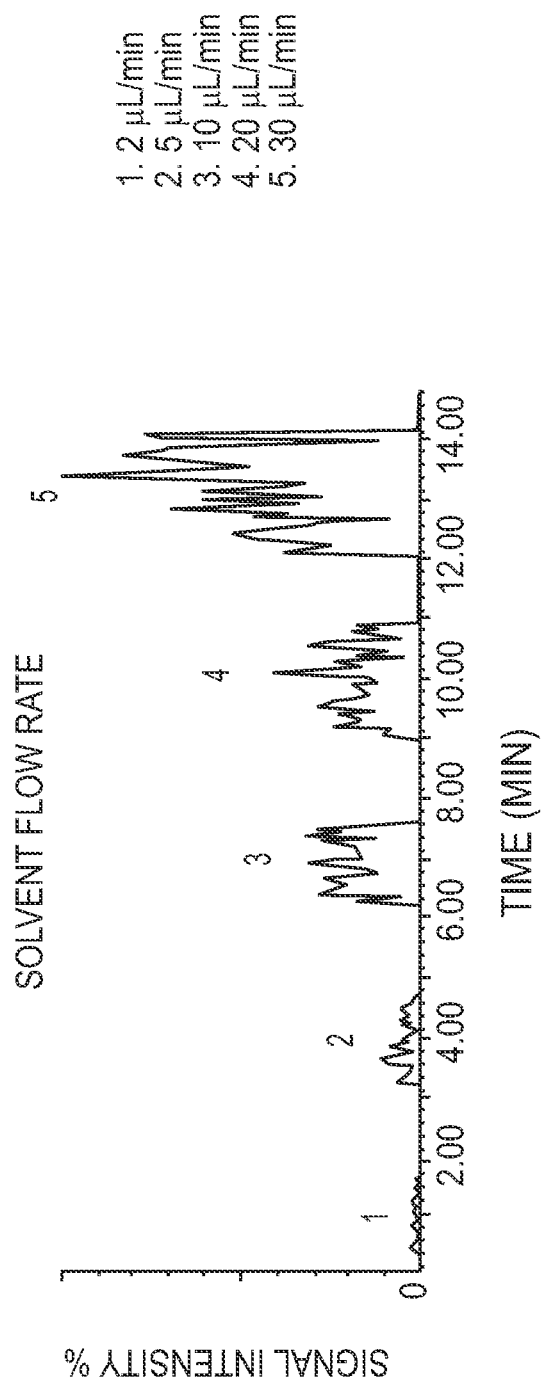

FIGS. 3A and 3B compare the signal intensity in a mass spectrum during analysis of a vacuum gas oil sample using a solvent mixture of toluene and acetonitrile (with 0.1 vol % of formic acid) at different ratios of non-polar to polar solvent and different solvent flow rates. In FIG. 3A, toluene to acetonitrile volume ratios of 2:1, 1:1, 1:2, and 1:5 were investigated. The solvent flow rate for the analysis in FIGS. 3A and 3B was 20 μl/min. As shown in FIG. 3A, the volume ratio of 1:5 provides the highest signal intensity. More generally, ratios of non-polar compound to polar compound in a solvent can be from about 2:1 to about 1:10, with ratios of about 1:2 or less being preferred, such as about 1:5 or less.

A relatively high flow rate is needed when analyzing samples on HP-TLC or source rocks. The reason is that the oil sample is retained by the HP-TLC plate or the rock matrix. To sample the oil at and below the top surface, stronger flow rate is required. The effect of flow rates on the signal level is shown in FIG. 3B.

For the mass spectrometry examples described herein, the desorption electrospray ionization-mass spectrometry (DESI-MS) analysis was performed using a DESI source built in house, which was coupled to a Waters Quattro II tandem quadrupole mass spectrometry system. The power supply controller was engaged to the interlock system. The syringe was placed inside of the interlock box. High voltage (such as about 5 kV) was applied at the needle of the syringe. The power supply controller also provided a reading for the voltage being applied to the syringe needle. For examples involving spatial profiling of a solid core, experiments were performed by manually moving the sample on the sample holder. The sample can be moved relative to the syringe at a rate of about 100 to about 500 micrometers/second. A spray impact angle of 52° was used. A source voltage of 5 kV was used and the nebulizing nitrogen gas pressure used was 150 psig. The MS scan speed was 2 s/scan; the MS resolution was unit mass resolution; the cone voltage was ramped from 20 to 70 V as mass was scanned from 70 to 1000 amu. As described above, different solvent systems and substrates were tested to achieve the best MS response. A mixture of toluene and acetonitrile (1:5 volume ratio) with 0.1 vol % of formic acid was used as the solvent at the flow rate of 20 μL/min on the HP-TLC substrates if not specified otherwise. The solvent spot size was about 400 μm when using toluene and acetonitrile (1:5 ratio) as the solvent at the flow rate of 20 μL/min.

Liquid Sample Characterization

Various vacuum gas oil cuts were tested using DESI-MS. Positive ion mode DESI was used to detect basic polar oil molecules and negative ion mode DESI was used to detect acidic polar oil molecules. As indicated with DESI analysis, the molecular weight distribution of the basic polar molecules moves toward the higher molecular weight range as the boiling point increases. The signal intensity is sufficient to allow for qualitative identification of the various compounds present within the vacuum gas oil cuts. This is expected and the result is consistent with traditional positive electrospray ionization (ESI). This demonstrates that a DESI method can achieve similar results to a conventional ESI method, even though the amount of sample preparation required for ESI is much greater than the sample preparation for DESI. Additionally, DESI can be used for direct surface analysis/profiling, such as analysis/profiling of a petroleum or hydrocarbon sample in a solid matrix.

Figure 4:
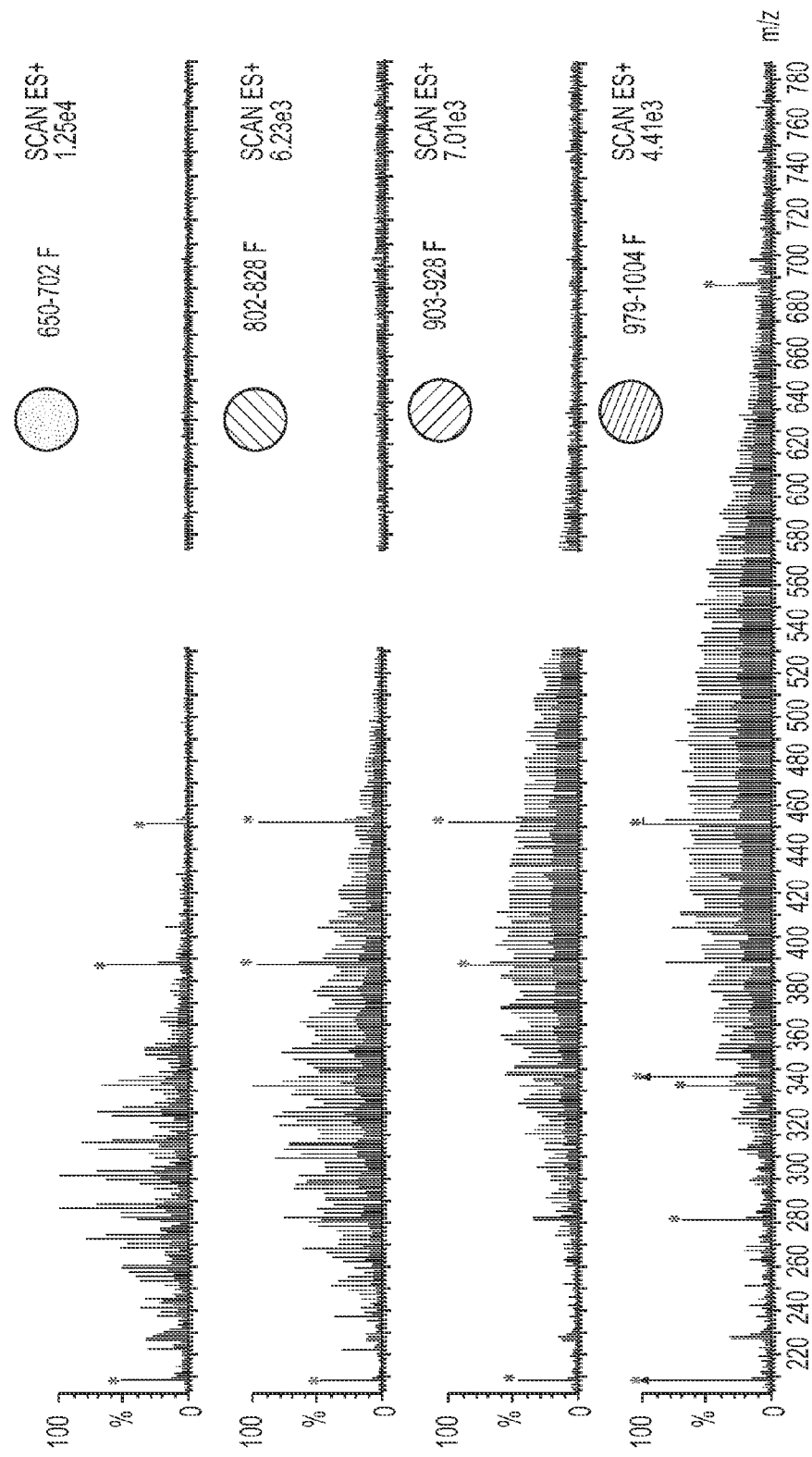
FIG. 4 shows mass spectra from positive ion desorption electrospray ionization-mass spectrometry for various boiling ranges for a single petroleum source.
Figure 5:
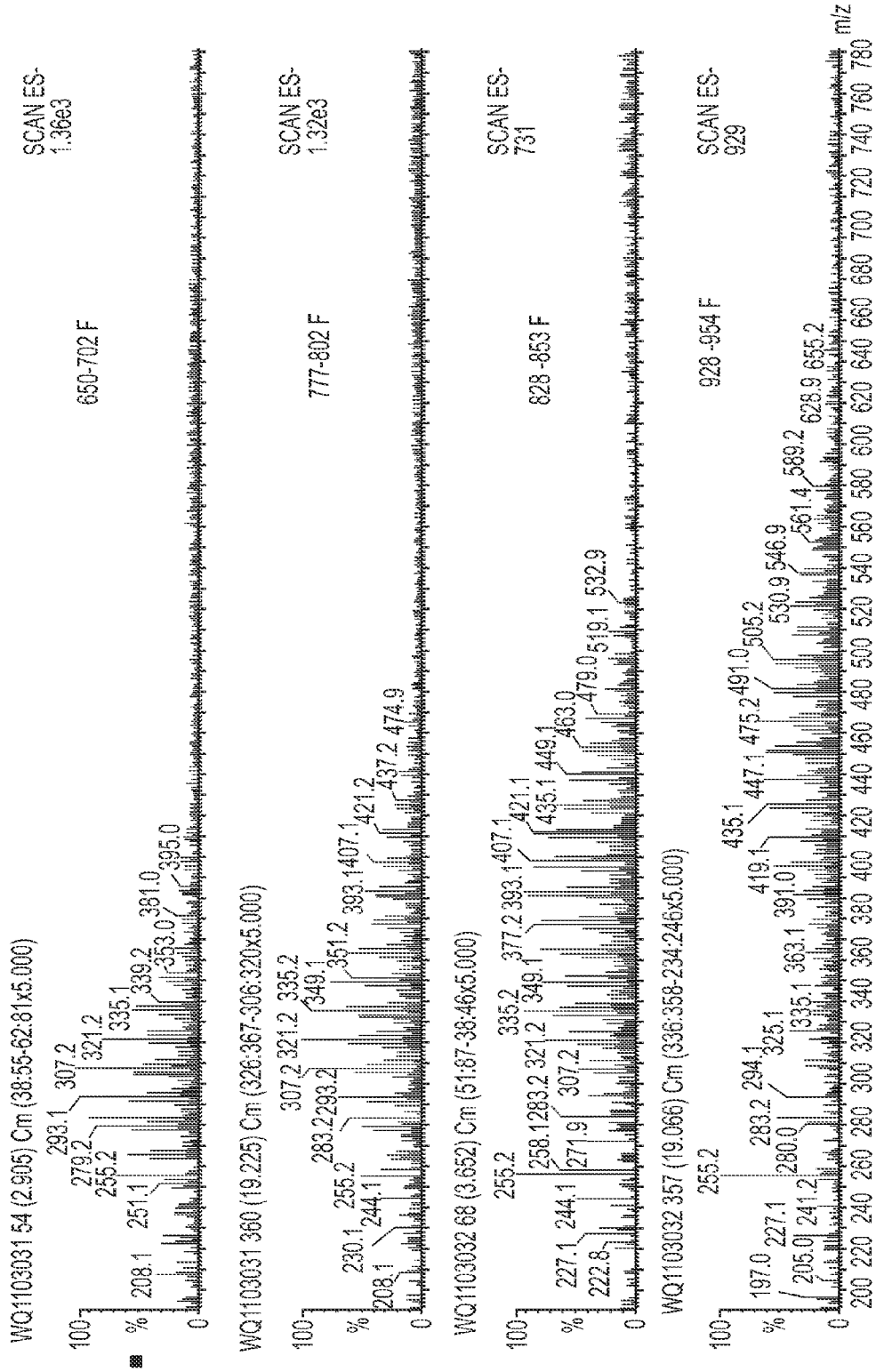
FIG. 5 shows mass spectra from negative ion desorption electrospray ionization-mass spectrometry for various boiling ranges for a single petroleum source.

FIG. 5 shows the negative ion DESI-MS for a group of vacuum gas oil boiling range cuts of the same crude oil used for the positive ion DESI-MS in FIG. 4. Acidic polar molecules were detected in the negative ion mode and again the results were consistent with a negative ion mode ESI of the same sample. This again indicates that DESI can provide reliable information for the molecular composition information of the polar molecules (both basic and acidic) of vacuum gas oil cuts.

Figure 6:
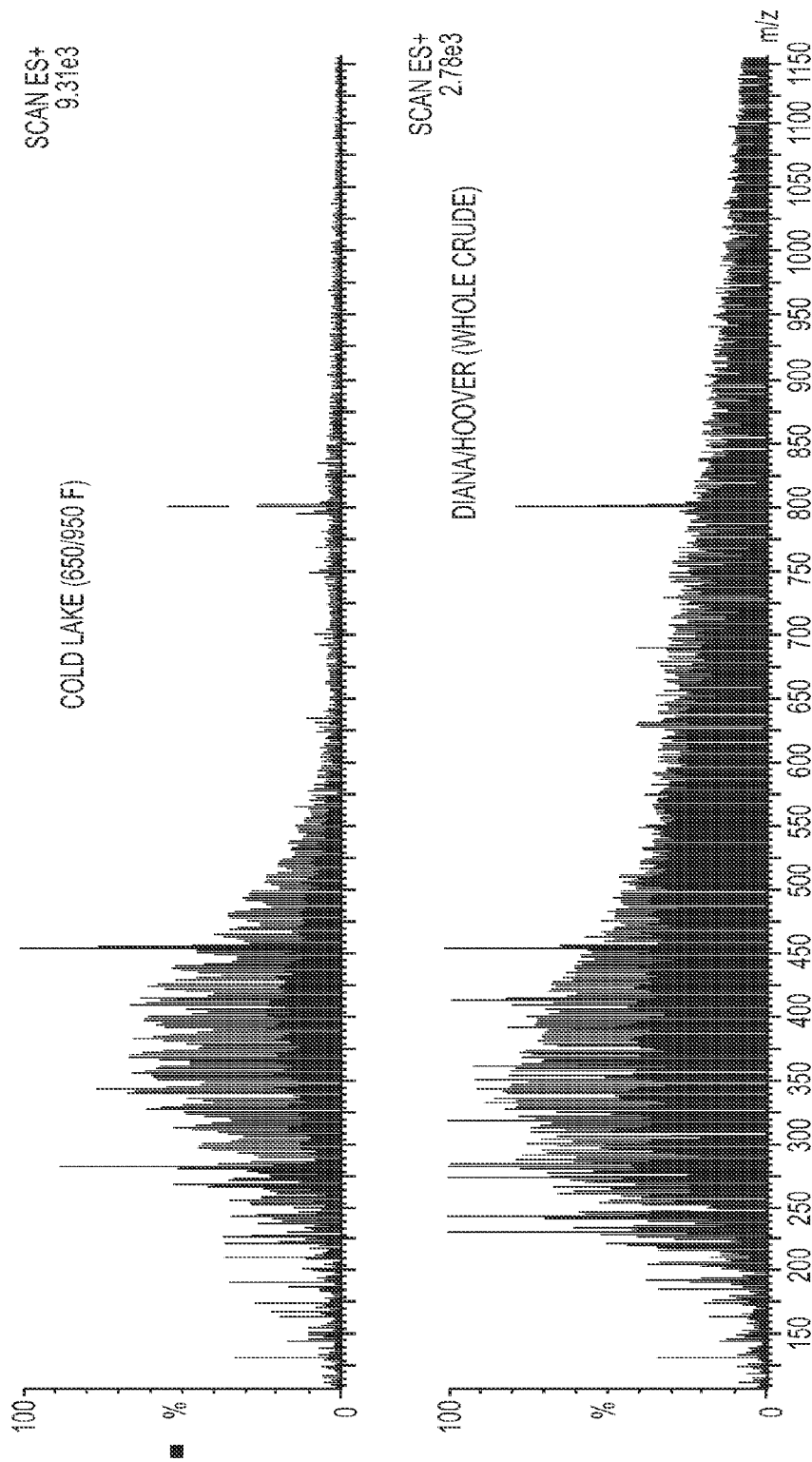
FIG. 6 shows mass spectra from positive ion desorption electrospray ionization-mass spectrometry for two different petroleum sources.

FIG. 6 shows DESI-MS spectrographs for samples from two additional petroleum sources. The upper spectrograph in FIG. 6 shows a DESI-MS spectrograph for a 650° F.-950° F. fraction from a second petroleum source. This approximately corresponds to a vacuum gas oil from a second petroleum source. As shown in the upper spectrograph in FIG. 6, the DESI-MS method is effective for qualitative identification of the polar species in a second type of petroleum with a different composition of polar compounds. The lower spectrograph in FIG. 6 shows that the DESI-MS technique is also effective whole crudes. The lower spectrograph in FIG. 6 is a positive ion mode DESI-MS spectrum of a whole crude from a third petroleum source. The whole crude in the lower spectrograph in FIG. 6 shows a broader molecular weight distribution of polar molecules of 160 to 1150 g/mol, in comparison with the molecular weight of the polar molecules in the vacuum gas oil in the upper spectrograph in FIG. 6 of 200 to 600 g/mol.

Solid Sample Characterization

Figure 7A:
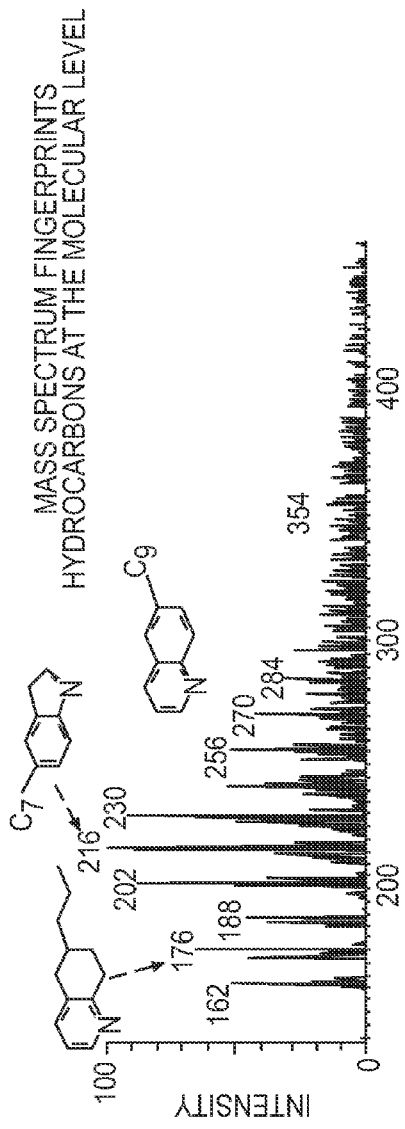
FIG. 7A and FIG. 7B show a mass spectrum and additional analysis for a hydrocarbon source in a solid matrix.
Figure 7B:
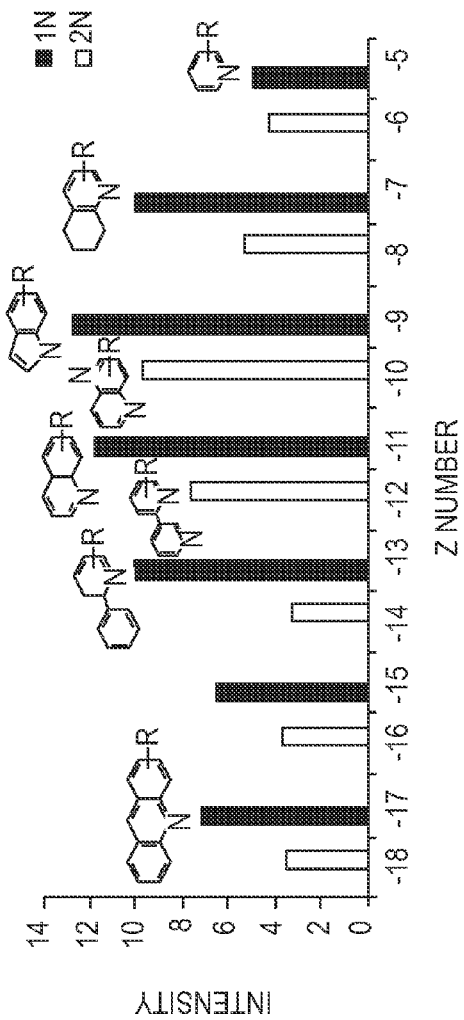

In addition to characterization of liquid samples, DESI-MS can also be used to fingerprint hydrocarbons in a solid matrix. For example, DESI-MS was used to fingerprint hydrocarbons at molecular level on the surface of source rocks and shale core samples. The data generated in FIGS. 7A and 7B was obtained using an apparatus similar to the apparatus schematically shown in FIG. 1. The oil in the core sample was solvated, desorbed, and detected with a mass spectrometer as the detector, providing the identification of hydrocarbon molecules. As described for the configuration shown in FIG. 1, the method left a "line" on the core sample after scanning with the DESI solvent spray. The formation of the "line" was due to the depletion of oil from the rock surface by the DESI solvent spray. The mass spectrometer provides a mass spectrum with polar hydrocarbon signature peaks over a mass range roughly corresponding to a vacuum gas oil fraction, as shown in FIG. 7A. The mass spectrum can then be analyzed to identify the compounds within the mass spectrum. Because the mass spectrum provides sufficient qualitative resolution, various types of compositional information can be determined. FIG. 7B shows a Z number (unsaturation) distribution and a molecular core structure for the hydrocarbons in the shale sample, which are examples of compositional analysis.

In addition to general compositional analysis, DESI-MS can be used to scan or spatially profile a petroleum (or hydrocarbon) sample in a solid matrix, such as hydrocarbons in source rocks, shale cores, and/or various types of sedimentary rocks. Scanning a solid matrix sample using the DESI-MS technique can be done to provide a one-dimensional spatial distribution of individual molecules on or near the surfaces of solid matrix samples.

Figure 8:
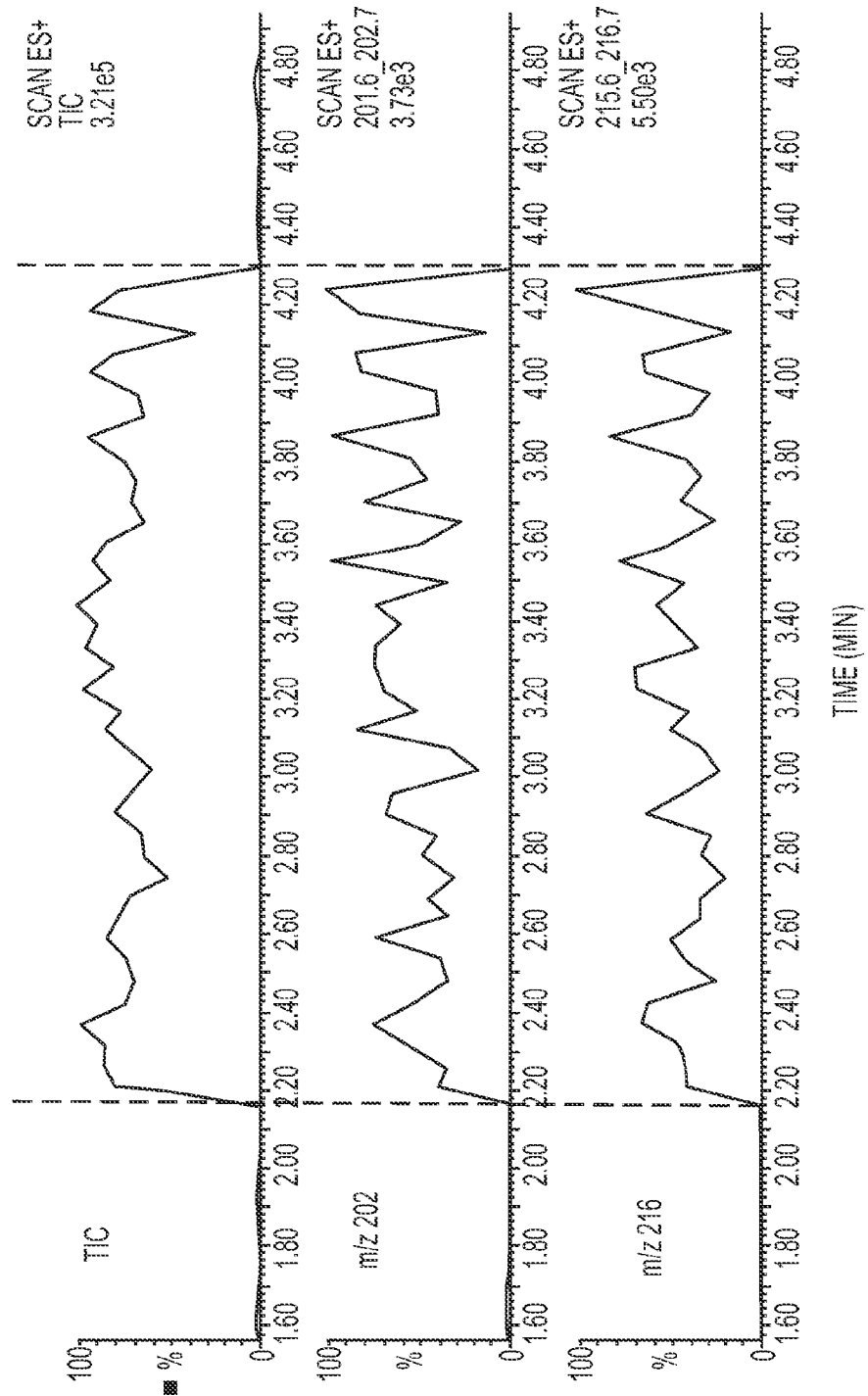
FIG. 8 shows mass spectra for spatial profiling of hydrocarbons in a solid matrix.

FIG. 8 shows results from analysis of another core sample from the shale source used in FIGS. 7A and 7B. The sample used to generate the data in FIG. 8 was scanned along a depth direction of the sample to obtain a profile length of 33 mm. The scanning of the core sample 33 mm in length took about 2 minutes. The sample was manually moved at the speed of about 275 μm/min. The vertical dotted lines in FIG. 8 show the alignment of the chromatographs with respect to time (and therefore with respect to depth along the shale core sample). The top mass spectrum in FIG. 8 shows the total ion chromatogram (TIC) over the 2 minutes scanning of shale core sample. The middle and bottom mass spectrums in FIG. 8 show the ion chromatograms of ions at selected mass to charge ratios of m/z=202 and m/z=216 along the core sample. As shown in FIG. 8, the distribution of the ions at the selected mass to charge ratios is relatively homogeneous over the profile distance. By comparing the ion chromatograms with the corresponding depth in the core sample, the intensity variation of ions along the core sample can be determined, and the spatial distribution of a specific ion can be provided.

Figure 9:
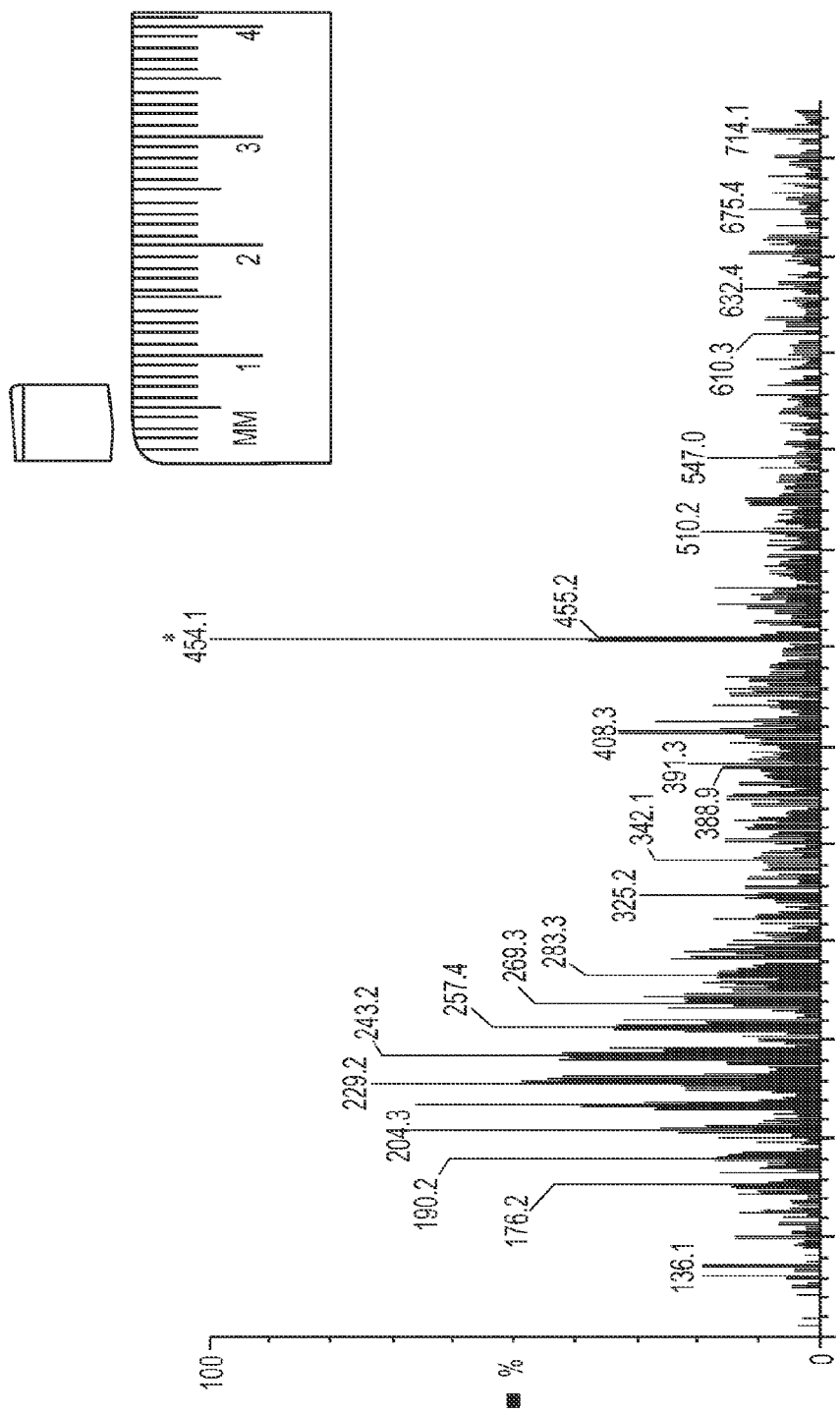
FIG. 9 shows a mass spectrum from analysis of another sample in a solid matrix.

DESI-MS analysis was also performed on a shale core sample from a second shale source. A 7×7 mm sample from the second shale source was used for the analysis. The size of the sample is shown in the upper right corner of FIG. 9. When analyzing the core sample from the second shale source, it was found that polishing the surface of the sample improved the sensitivity of the MS detector. FIG. 9 shows the mass spectrum obtained by DESI-MS after polishing the core sample from the second shale source with 3M polish paper for about 30 seconds.

DESI-MS is applicable for the characterization of oil-stained rock surfaces. In this embodiment, the rock matrix is usually a sandstone or carbonate that contains little or no native organic matter and the analyte is oil that has migrated onto the rock surface.

ADDITIONAL EMBODIMENTS

Embodiment 1

A method for analyzing a hydrocarbon sample, comprising: preparing a hydrocarbon sample having a surface; impinging a solvent on the prepared hydrocarbon sample having a surface at an angle between about 30° and about 60° relative to the surface, the solvent comprising a stream of solvent droplets, the solvent comprising a non-polar compound and a polar compound; capturing droplets desorbed from the surface at an inlet conduit for a mass spectrometer, the captured droplets including one or more compounds from the hydrocarbon sample; and generating at least one mass spectrum based on the one or more compounds from the hydrocarbon sample.

Embodiment 2

The method of Embodiment 1, wherein preparing a hydrocarbon sample having a surface comprises obtaining a solid matrix containing a hydrocarbon sample.

Embodiment 3

The method of any of the above embodiments, wherein the hydrocarbon sample comprises a petroleum sample.

Embodiment 4

The method of any of the above embodiments, wherein the polar compound is acetonitrile, methanol, butanol, an alcohol containing 6 carbons or less, or a combination thereof.

Embodiment 5

The method of any of the above embodiments, wherein the non-polar compound is toluene, benzene, xylene, carbon tetrachloride, chloroform, methylene chloride, an aromatic hydrocarbon that does not contain heteroatoms, or a combination thereof.

Embodiment 6

The method of any of the above embodiments, wherein the solvent further comprises formic acid, an organic acid containing 4 carbons or less, or a combination thereof.

Embodiment 7

The method of any of the above embodiments, wherein the ratio of non-polar compound to polar compound in the solvent is 1:2 or less, preferably 1:4 or less.

Embodiment 8

The method of any of Embodiments 2-7, wherein preparing the hydrocarbon sample further comprises cutting the solid matrix to form the surface of the solid matrix, polishing the surface of the solid matrix prior to impinging the solvent on the surface, or a combination thereof.

Embodiment 9

The method of Embodiment 8, wherein the surface is polished to produce a solid matrix with a polished surface having a roughness of about 1 mm or less.

Embodiment 10

The method of any of the above embodiments, wherein impinging the solvent on the surface of the solid matrix comprises scanning the solvent along a direction relative to the surface of the solid matrix, a rate of scanning along the direction relative to the surface of the solid matrix preferably being from about 100 micrometers to about 500 micrometers per second, the scanning direction relative to the surface of the solid matrix optionally but preferably comprising a depth for the solid matrix.

Embodiment 11

The method of Embodiment 10, wherein generating at least one mass spectrum comprises generating one or more mass spectra corresponding to a profile along the scanning direction for at least one compound from the hydrocarbon sample.

Embodiment 12

The method of any of the above embodiments, wherein preparing a hydrocarbon sample comprises depositing a liquid hydrocarbon sample on a substrate to form the hydrocarbon sample having the surface.

Embodiment 13

The method of Embodiment 12, wherein the substrate comprises a silica gel.

Embodiment 14

The method of Embodiment 13, wherein the hydrocarbon sample further comprises a preparation solvent, the preparation solvent preferably comprising toluene.

What is claimed is:

1. A method for analyzing a hydrocarbon sample, comprising:
   obtaining a solid matrix containing a hydrocarbon sample; wherein the solid matrix comprises one of source rocks, reservoir rocks, oil shale, sedimentary rocks, or a core sample taken from a potential or existing well location or shale extraction location;
   impinging a solvent on a surface of the solid matrix at an angle between about 30° and about 60° relative to the surface, the solvent comprising a stream of solvent droplets, the solvent comprising a non-polar compound and a polar compound;
   capturing droplets desorbed from the surface of the solid matrix at an inlet conduit for a mass spectrometer, the captured droplets including one or more compounds from the hydrocarbon sample; and
   generating at least one mass spectrum based on the one or more compounds from the hydrocarbon sample.

2. The method of claim 1, wherein the hydrocarbon sample comprises a petroleum sample.

3. The method of claim 1, wherein the polar compound is acetonitrile, methanol, butanol, an alcohol containing 6 carbons or less, or a combination thereof.

4. The method of claim 1, wherein the non-polar compound is toluene, benzene, xylene, carbon tetrachloride, chloroform, methylene chloride, an aromatic hydrocarbon that does not contain heteroatoms, or a combination thereof.

5. The method of claim 1, wherein the solvent further comprises formic acid, an organic acid containing 4 carbons or less, or a combination thereof.

6. The method of claim 1, wherein the ratio of non-polar compound to polar compound in the solvent is 1:2 or less.

7. The method of claim 1, wherein impinging the solvent on the surface of the solid matrix comprises scanning the solvent along a direction relative to the surface of the solid matrix.

8. The method of claim 7, wherein a rate of scanning along the direction relative to the surface of the solid matrix is from about 100 micrometers to about 500 micrometers per second.

9. The method of claim 7, wherein generating at least one mass spectrum comprises generating one or more mass spectra corresponding to a profile along the scanning direction for at least one compound from the hydrocarbon sample.

10. The method of claim 1, wherein the polar compound is acetonitrile, methanol, butanol, an alcohol containing 6 carbons or less, or a combination thereof; the nonpolar compound is toluene, benzene, xylene, carbon tetrachloride, chloroform, methylene chloride, an aromatic hydrocarbon that does not contain heteroatoms, or a combination thereof; and the solvent further comprises formic acid, an organic acid containing 4 carbons or less, or a combination thereof.

11. A method for analyzing a hydrocarbon sample, comprising:
   obtaining a solid matrix containing a hydrocarbon sample;
   cutting the solid matrix to form a surface of the solid matrix;
   impinging a solvent on the surface of the solid matrix at an angle between about 30° and about 60° relative to the surface, the solvent comprising a stream of solvent droplets, the solvent comprising a non-polar compound and a polar compound;
   capturing droplets desorbed from the surface of the solid matrix at an inlet conduit for a mass spectrometer the captured droplets including one or more compounds from the hydrocarbon sample; and
   generating at least one mass spectrum based on the one or more compounds from the hydrocarbon sample.

12. A method for analyzing a hydrocarbon sample, comprising:
   obtaining a solid matrix containing a hydrocarbon sample;
   polishing a surface of the solid matrix prior to impinging a solvent on the surface;
   impinging the solvent on the surface of the solid matrix at an angle between about 30° and about 60° relative to the surface, the solvent comprising a stream of solvent droplets, the solvent comprising a non-polar compound and a polar compound;
   capturing droplets desorbed from the surface of the solid matrix at an inlet conduit for a mass spectrometer, the captured droplets including one or more compounds from the hydrocarbon sample; and
   generating at least one mass spectrum based on the one or more compounds from the hydrocarbon sample.

13. The method of claim 12, wherein the surface is polished to produce a solid matrix with a polished surface having a roughness of about 1 mm or less.

14. A method for analyzing a hydrocarbon sample, comprising:
   obtaining a solid matrix containing a hydrocarbon sample;
   impinging a solvent on a surface of the solid matrix at an angle between about 30° and about 60° relative to the surface, the solvent comprising a stream of solvent droplets, the solvent comprising a non-polar compound and a polar compound; wherein impinging the solvent on the surface of the solid matrix comprises scanning the solvent along a direction relative to the surface of the solid matrix; wherein the scanning direction relative to the surface of the solid matrix comprises a depth for the solid matrix;
   capturing droplets desorbed from the surface of the solid matrix at an inlet conduit for a mass spectrometer, the captured droplets including one or more compounds from the hydrocarbon sample; and
   generating at least one mass spectrum based on the one or more compounds from the hydrocarbon sample.

15. A method for analyzing a hydrocarbon sample, comprising:
   preparing a hydrocarbon sample having a surface wherein preparing a hydrocarbon sample comprises cutting a solid matrix containing the hydrocarbon sample to form the hydrocarbon sample having a surface;
   impinging a solvent on the prepared hydrocarbon sample having a surface at an angle between about 30° and about 60° relative to the surface, the solvent comprising a stream of solvent droplets, the solvent comprising a non-polar compound and a polar compound;
   capturing droplets desorbed from the surface at an inlet conduit for a mass spectrometer, the captured droplets including one or more compounds from the hydrocarbon sample; and
   generating at least one mass spectrum based on the one or more compounds from the hydrocarbon sample.

* * * * *